(12) United States Patent
Doerr et al.

(10) Patent No.: US 8,417,339 B2
(45) Date of Patent: Apr. 9, 2013

(54) SYSTEM FOR THE REMOTE PROGRAMMING OF A PERSONAL MEDICAL DEVICE

(75) Inventors: Thomas Doerr, Berlin (DE); Joachim Reinke, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1276 days.

(21) Appl. No.: 12/167,311

(22) Filed: Jul. 3, 2008

(65) Prior Publication Data

US 2009/0018598 A1    Jan. 15, 2009

(30) Foreign Application Priority Data

Jul. 10, 2007    (DE) .......................... 10 2007 032 469

(51) Int. Cl.
*A61N 1/08* (2006.01)
(52) U.S. Cl. ........................................................ 607/30
(58) Field of Classification Search .................... 607/30, 607/31, 59, 60
See application file for complete search history.

(56) References Cited

U.S. PATENT DOCUMENTS

| | | | |
|---|---|---|---|
| 6,442,433 B1 | 8/2002 | Linberg | |
| 6,880,085 B1 | 4/2005 | Balczewski et al. | |
| 7,096,067 B2 | 8/2006 | Linberg | |
| 7,460,910 B2 * | 12/2008 | Webb | ............................ 607/30 |
| 2002/0032470 A1 | 3/2002 | Linberg | |
| 2002/0095196 A1 | 7/2002 | Linberg | |
| 2003/0014090 A1 | 1/2003 | Abrahamson | |
| 2003/0144711 A1 | 7/2003 | Pless et al. | |
| 2004/0039651 A1 | 2/2004 | Grunzig et al. | |
| 2005/0204134 A1 | 9/2005 | Von Arx et al. | |
| 2006/0189854 A1 | 8/2006 | Webb | |

FOREIGN PATENT DOCUMENTS

| | | |
|---|---|---|
| EP | 1 075 161 A | 2/2001 |
| WO | WO 01/03575 A | 1/2001 |
| WO | WO 2006/029425 A | 3/2006 |

OTHER PUBLICATIONS

Amine, B. "Authentifizierung und Identitätsmanagement" Internet Article. Sicherheit und Technischer Datenschutz In Informationissystem. Seminar I, Sommersemester 2006 AM IPD—Lehrstuhl Prof Böhm, [Online] Jun. 26, 2006, Seiten 1-18, XP002501955 Gefundem im INternet: URL:http://www.ipd.uka.de/{00sem/SecIS06/Ausarbeitungen/Seminarausarbeitung-Benchaalal-AuthentifizierungundIdManagement.pdf> [gefundem am Oct. 29, 2008].

Ueckert F. et al., "Empowerment of patients and communication with health care professionals through an electronic health record" International Journal of Medical Informatics, Elsevier Scientific Publishers, Shannon, IR, Bd. 70, Nr 2-3, (Jul. 1, 2003), Seiten 99-108 XP004444247, ISN: 1386-5056.

Koopman, G., Mobile Transaktionsnummern (TAN), IP.COM Journal, IP.COM Inc., West Henrietta, NY, US, Jul. 23, 2003.

European Search Report for European Patent Application No. 08159444.2-2001 / 2031532, Jul. 17, 2009.

\* cited by examiner

*Primary Examiner* — Eric D. Bertram
(74) *Attorney, Agent, or Firm* — Craig A. Fieschko, Esq.; DeWitt Ross & Stevens S.C.

(57) ABSTRACT

The invention comprises a system and a method for secure remote programming of an implant. For this purpose, a TAN list is generated on the part of the programming device and both stored in the implant (10) and also provided to a physician. The TAN list is preferably indexed and the implant predefines the index of a TAN in each case, which a physician must input to have a programming instruction executed by the implant.

20 Claims, 4 Drawing Sheets

SYSTEM FOR THE REMOTE PROGRAMMING OF A PERSONAL MEDICAL DEVICE

BACKGROUND OF THE INVENTION

The invention relates to a system for the remote programming of a personal medical device, in particular an implantable medical device, such as a cardiac pacemaker, a defibrillator, or the like.

Cardiac pacemakers or defibrillators are sometimes used in combination with a central service center, wherein medical, physiological, or operational data obtained by the cardiac pacemaker or defibrillator is transmitted to the central service center to analyze the data and provide it to an attending physician via a corresponding user interface.

Some functions of such implants are controlled by software or firmware and are programmable. It often occurs that after initial programming, further programming or reprogramming is desirable shortly before, during, or after the implantation to be able to better adjust the implant to health states of a patient which have possibly changed in the meantime, or to increase the performance of the implant in another manner. Programming or reprogramming of this type is frequently performed by a physician with the aid of a programming device via a short-range, wireless data link through which the physician programs a selected implant in regard to the patient.

However, programming or reprogramming of the implant may also be performed remotely, for example, via the central service center. As an example, a data link may be produced for this purpose between the service center and an intermediate intermediate patient device located in proximity to a patient, with a bidirectional data link being generated between the implant and the intermediate patient device. The connection between the service center and intermediate patient device may be implemented as wirelessly or otherwise, for example, via the telephone network, the Internet, or similar data lines.

A problem exists in this case of ensuring that the selected implant and/or the intermediate patient device is not reprogrammed as a result of an erroneous data transmission, or by unauthorized reprogramming or misuse.

To solve this problem, encrypting and/or verifying programming instructions for the programming or reprogramming of an implant using a public-key encryption method, such as PGP, is provided according to U.S. Pat. No. 6,442,432.

SUMMARY OF THE INVENTION

The present invention is based on the object of ensuring verification of programming instructions in an alternative manner, so that a programming instruction to a personal device, such as an implant or a intermediate patient device, is authentic and originates from an authorized source.

One version of the invention involves a system of the type previously noted, which, in addition to the personal device (the implant or intermediate patient device), a programming device assigned to the personal device contains a transaction number (TAN) list generator. The programming device is implemented to generate a list having transaction numbers (TAN) and to transmit this TAN list to the personal device and to a further device accessible to a physician, or to print it out directly.

The system thus includes a programmable personal device, particularly an active medical implant such as a cardiac pacemaker or a cardioverter/defibrillator, as well as a programming device and a central service center. The programmable personal device may be programmed directly or, for example, via a short-range wireless data communication link with the aid of the programming device, or remotely via the service center. For this purpose, the programmable personal device has a first data communication interface for at least indirect connection of the personal programmable device to the service center, as well as a second data communication interface which is separate from the first data communication interface and which is implemented to allow direct wireless data communication between the personal device and the programming device.

The service center has a data communication interface for at least indirect connection of the service center to the personal device and a user interface, which is implemented to accept programming instructions for the programmable personal device so that the programming instructions may be transmitted to the personal device via the service center.

The programming device has at least one data communication interface which is compatible with the second data communication interface of the personal device, and which allows direct wireless data communication to be performed between the programming device and the personal device.

The programming device also has a TAN list generator which is implemented to generate a TAN list and to transmit it on one hand to the personal device and on the other hand either to a TAN server, or to a personal communication device of a physician, such as a mobile telephone, a fax machine, or an e-mail client, or to print it out on a printer.

The service center is then used when the personal device is to be remotely programmed, with the programming instructions being secured using a TAN. The service center preferably requests the input of a TAN for every programming instruction, and appends the TAN to the programming instruction. The service center subsequently transmits the programming instruction together with the TAN to the personal device. The personal device is implemented to compare the next TAN stored in its memory with the TAN which is appended to a particular received programming instruction. The personal device is then further implemented to execute a programming instruction only when the two TAN correspond and otherwise to ignore or delete the programming instruction.

The TAN list generator of the programming device is preferably implemented for the purpose of determining an associated index for every generated TAN, jointly called iTAN, and to add TAN and index to a list. In another version of the invention, the programming device is implemented to generate TAN without an index and also to add the TAN to a list. The generated TAN list may thus contain iTAN, TAN, or both.

The programming device is also implemented for the purpose of transmitting the TAN list or iTAN list thus generated either to a TAN server or to a personal communication device such as a mobile telephone, fax machine, or e-mail client, or to print it out.

Upon verification using iTAN lists, it is advantageous if the personal device, e.g., the implant, is implemented, after receiving a iTAN list or after the execution of a programming instruction, to determine an index for a subsequent programming instruction and transmit it to the service center.

The service center is preferably implemented in combination with a service user interface to query an iTAN for every programming instruction, so that a physician is requested to input the TAN belonging to the index. The service center appends the TAN to the programming instruction and transmits the programming instruction to the personal device. If the physician has specified the correct TAN and/or the TAN belonging to the specified index, the personal device may execute the programming instruction. Otherwise, the programming instruction is ignored.

The user interface is preferably implemented as a remote programming application executable remotely from the service center and connected to the service center. This allows the remote programming of an implant to be performed from the physician's computer via the service center.

The system advantageously has a physically separate and spatially remote TAN server as a further component. The programming device then has a further data communication interface, to be able to transmit a TAN list to the TAN server, in addition to the data communication interface for the direct data exchange with the personal device. The TAN server preferably has a databank which contains entries for a user identification; a personal device assigned to the user identification, identified by its device identification; and a message address of an addressable communication device assigned to the user identification. Furthermore, the TAN server has a TAN user interface which is implemented to accept inputs of the user and to assign the inputs to a user identification and relay them assigned in this manner to the TAN server. A further component of the TAN server is preferably a message interface via which the TAN server may transmit a TAN to an addressable communication device such as a mobile telephone, an e-mail client, or a fax machine, which is identified by its message address. The TAN server also preferably has at least one data communication interface to be able to receive TAN lists from the programming device.

The TAN server is implemented to receive a TAN query assigned to a user identification and subsequently to generate a TAN message and transmit it via the message interface to the addressable communication device assigned via the databank entries of the user identification of the querying user. The TAN server thus makes it possible for a physician to avoid the need to store and maintain a TAN list generated by the programming device. Rather, this is performed via the TAN server.

In a version of the invention having indexed TAN, the TAN query to the TAN server additionally contains the last index determined by the personal device for the TAN to be input, in addition to the user identification and the device identification.

The TAN server is preferably completely separate from the service center administratively and spatially.

The object on which the invention is based is additionally also achieved by a programming device designed in the meaning of the system according to the invention, i.e., concretely a programming device having a TAN list generator, and by a personal device also designed in the meaning of the invention. The personal device is particularly an active medical implant which is implemented to store TAN lists including indices and to determine the index of a TAN in a timely manner before a new programming instruction, which is then to be appended to the programming instruction, so that the personal device also executes the programming instruction.

Furthermore, invention encompasses a method which has at least some of the following steps:
provision of an implant (10), and a programming device (70) uniquely assigned to the implant for the duration of the programming procedure;
generation of a TAN list with associated indices, or without indices, by the programming device (70);
transmission of the TAN list with indices, or without indices, to the implant (10) and a third device;
for TAN lists having indices, determination of an index by the implant;
composition of a programming instruction;
for TAN lists having indices, querying of a TAN with indication of the index determined by the implant;
appending a TAN to the programming instruction, and transmission of the programming instruction to the implant;
for TAN lists having indices, comparison of the TAN stored in the implant and belonging to the index last determined by the implant to the TAN contained in the programming instruction;
execution of the programming instruction if the TAN are identical, or
ignoring or deleting the programming instruction if the TAN are not identical;
acknowledgement of success or failure of the execution of the programming instruction.

Further advantageous design variants result through combination of the features of various claims, or from the following description of an exemplary version of the invention.

BRIEF DESCRIPTION OF THE DRAWINGS

The invention will be explained in greater detail on the basis of an exemplary version with reference to the figures, which include.

DETAILED DESCRIPTION OF PREFERRED VERSIONS OF THE INVENTION

Figure 1:
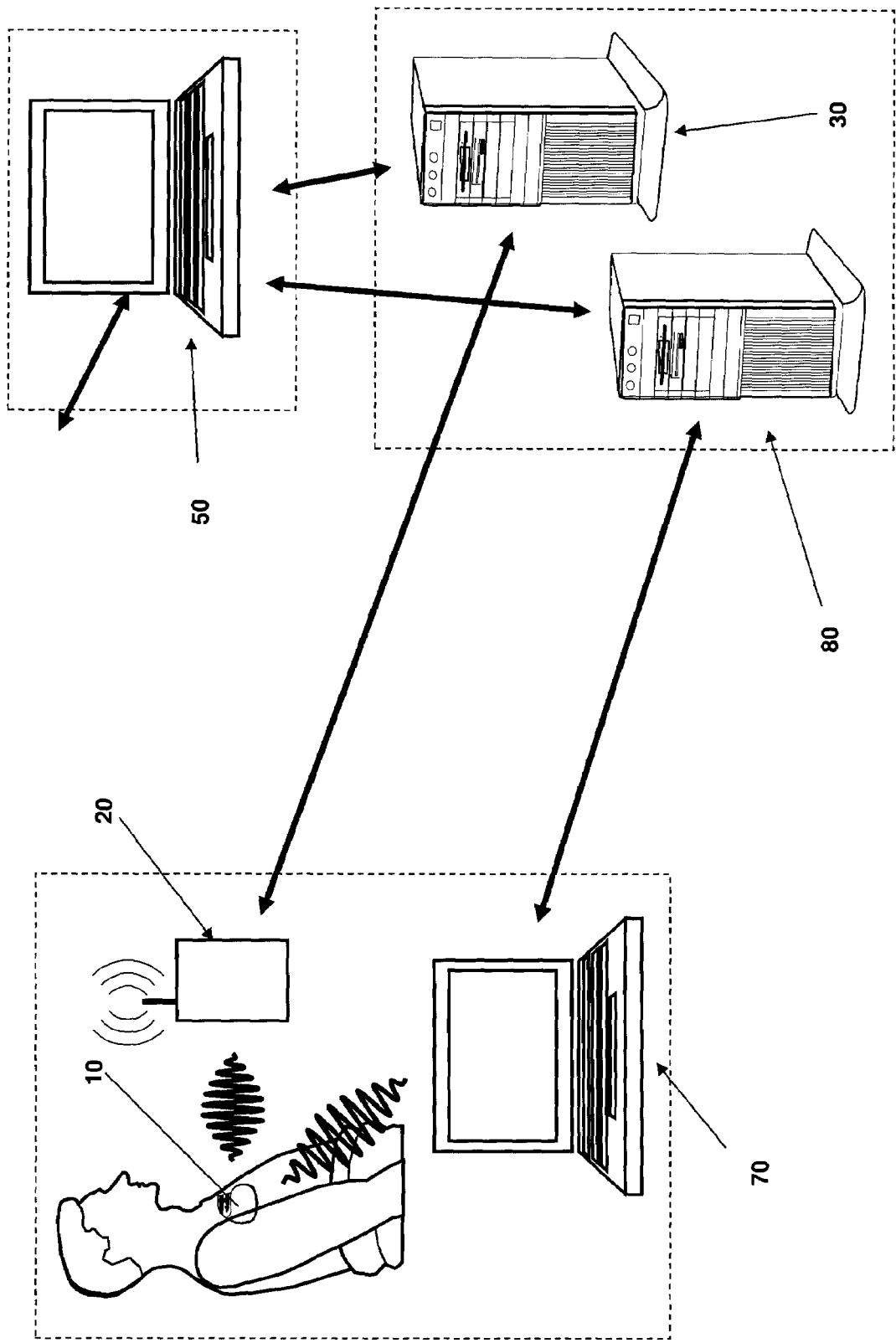
FIG. 1: shows an overview of a system for remote programming of an implant.

FIG. 1 shows the components of an exemplary system for remote programming of implants.

Figure 2:
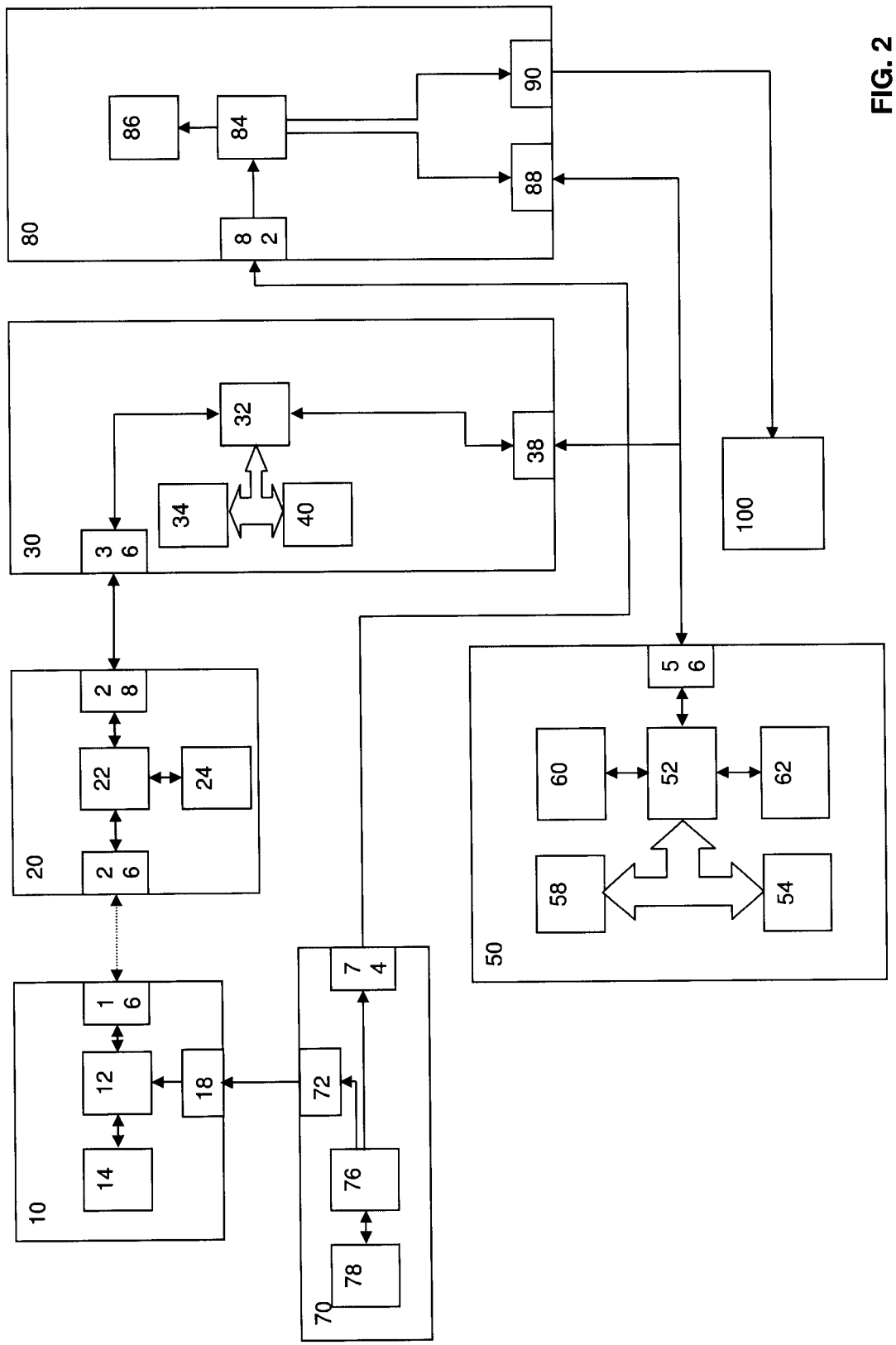
FIG. 2: shows block diagrams of the components of the system from FIG. 1.

One component is the implant 10 itself. It has a controller 12 (see FIG. 2) which is connected to both a memory 14 and also a telemetry unit 16. The telemetry unit 16 allows a wireless, bidirectional data transmission from and to the implant 10 containing it.

A further component is a intermediate patient device 20, which also has a controller 22, which is connected to a memory 24 and a first telemetry unit 26 for a bidirectional data transmission from and to the implant 10, and to a second data communication interface 28, via which the intermediate patient device 20 containing it may exchange data bidirectionally with a central service center 30.

In addition to a controller 32, the central service center 30 has a central databank 34 and a first data communication interface 36, via which the service center 30 may exchange data bidirectionally with the intermediate patient device 20. Moreover, the central service center 30 has a remote programming server unit 40, which is connected to both the control unit 32 of the service center and also to an Internet interface 38 for connection of a remote programming client 50.

The remote programming client 50 also has a central control unit 52, which is connected to a memory 54 and a data communication interface 56 for a bidirectional data communication with the service center 30. In addition, the remote programming client 50 has a remote programming application 58, which may be executed with the aid of the central control unit 52 and the memory 54. The remote programming application 58 is either executable as a stand-alone solution exclusively on the remote programming client 50 or, as a server application, also partially or entirely makes use of the central service center 30 and its remote programming server unit 40.

The remote programming application 58 allows programs to be composed on the remote programming client 50, which are executable for the implant 10 and its controller 12. The programs thus composed may be transmitted in the form of a programming instruction from the central service center 30 via the intermediate patient device 20 to the implant 10.

To display illustrations generated by the remote programming application, the remote programming client 50 has a display 60. In addition, an input unit 62 is provided so that a user, such as a physician, may make inputs for the remote programming of the implant 10.

The implant 10 and the intermediate patient device 20 are spatially located in and in proximity to a patient, respectively. The central service center 30 is positioned at a central location. The remote programming client 50 is located in proximity to a physician and may be very remote from the service center 30.

The system additionally includes a programming device 70 which has a first data communication interface 72 by which the programming device 78 may perform a short-range wireless data communication with the implant 10. In addition, the programming device 70 has a second data communication interface 74 via which the programming device 70 may be connected, for example, to a TAN server 80 or alternatively also to the service center 30 or the remote programming client 50. The programming device 78 has a controller 76 and a TAN list generator 78 in addition to the typical components of a programming device of this type.

Using the TAN list generator 78, the programming device 70 may generate indexed or non-indexed lists of transaction numbers (iTAN/TAN) and transmit them via the controller 76 and the data communication interface 72 on one hand to the implant 10 and on the other hand to the TAN server 80.

The implant 10, in addition to the data communication interface 16 for the data communication with the intermediate patient device 20, has a data communication interface 18, which is used for the short-range data communication between the programming device 70 and the implant 10. The implant 10 may receive an indexed TAN list via this data communication interface 18 and store it in its memory 14.

The indexed or non-indexed TAN list is additionally transmitted by the programming device 70 to the TAN server 80. For this purpose, the TAN server 80 has an input 82 which is connected to a controller 84 of the TAN server 80. The controller 84 of the TAN server 80 is in turn connected to a memory 86 of the TAN server 80. This memory 86 comprises a databank which has entries for a TAN list received from the programming device 70, as well as entries for a user identification, a device identification, and a message address assigned to these entries. A user is identified via the user identification. The device identification identifies the implant 10, and the message address is the address of a personal communication device such as a mobile telephone, a fax machine, or an e-mail client. The TAN server 80 may be connected to the remote programming client 50 via an output 88.

The TAN server 80 uses a second output 90 for transmitting messages, which are each identified by message addresses, to an addressable communication device 100 such as a fax machine, a mobile telephone, etc.

A user may retrieve a TAN list stored in the memory 86 of the TAN server 80 with the aid of a corresponding application on the remote programming client 50. For this purpose, the user must preferably input his user identification and the device identification of the implant to be programmed, because the TAN lists are implant-specific. The user has previously been accredited on the TAN server 80, so that the TAN server 80 now transmits a list having TAN to the communication device, which is assigned via the assignment of the message address to the remaining entries in the databank of the user.

To program the implant 10 remotely, the remote programming application 58 also requires, after the input of a programming instruction, the input of a TAN which corresponds to the index which the implant 10 has predefined. This index is determined by the implant 10 and transmitted via the intermediate patient device 20 to the service center 30, and from there to the remote programming application 58.

After completing a programming instruction, the user must now input the corresponding TAN and may receive this by retrieval of a TAN from the TAN server 80 or may take it from an expression previously prepared using the programming device 70. If the TAN thus appended to the programming instruction corresponds to the TAN stored in the implant 10, possibly under the corresponding index, the implant 10 may execute the programming instruction after receipt. Otherwise, the implant 10 will ignore the programming instruction.

Figure 3:
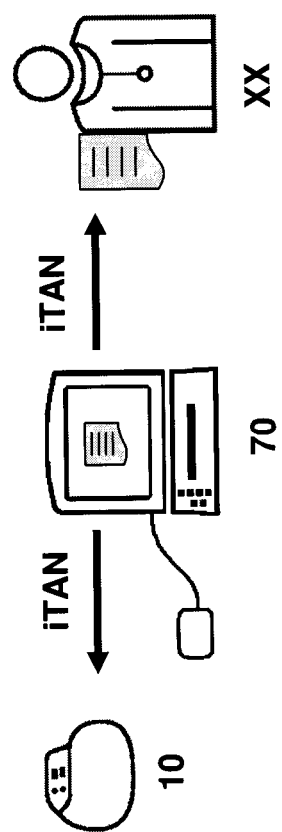
FIG. 3: shows the method for activating of the remote programming.
Figure 4:
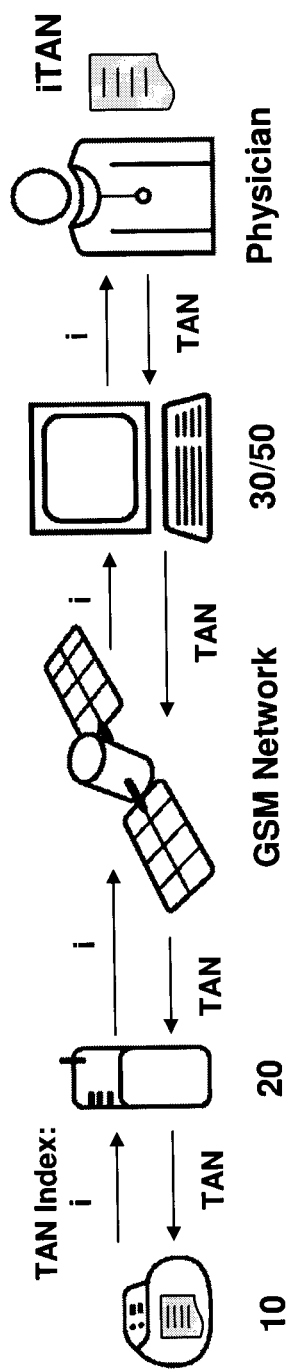
FIG. 4: shows the sequence of remote programming.

The procedures for generating a TAN list (FIG. 3) and remote programming (FIG. 4) are explained schematically once again in following FIGS. 3 and 4.

The method for activating the remote programming is shown in FIG. 3. A TAN/iTAN server is integrated in the programming device 70, which may generate transaction numbers and indexed transaction numbers (TAN/iTAN). This server transmits an indexed list having TAN numbers to the electronic implant 10 at the request of the physician 200 via the remote programming server 50 and after completed transmission to the electronic implant 10 provides this list to the physician in the form of a printout and optionally as a file.

The sequence of remote programming is shown in FIG. 4. The electronic implant 10 transmits the index of the next TAN required for remote programming from the stored list via intermediate patient device 20 and network service provider (e.g., GSM provider) to the service center 30 using regular data transmission. If the physician initiates remote programming, he is requested by the service center to input the TAN with the index i from the TAN list. This TAN is then transmitted jointly with the programming parameters as a component of a programming instruction for the remote programming to the electronic implant.

The electronic implant 10 checks the transmitted TAN and accepts the remote programming only if the transmitted TAN corresponds to the transmitted TAN of the TAN stored in the implant having the index i. Furthermore, the "used" TAN having the index i is marked as used and the next TAN index is determined via random generator or another similar method in the electronic implant 10 and communicated to the service center 30.

If all TAN are used, the remote programming in the electronic implant 10 is deactivated and this state is communicated to the service center 30. It is then only possible to reactivate the remote programming via the mechanism from FIG. 3.

What is claimed is:

1. A system for the remote programming of a programmable personal medical device (10), in particular an implantable medical device such as a cardiac pacemaker, defibrillator, or the like, including:

I. a programmable personal device (10), and

II. a programming device (70), wherein:
a. the programmable personal device (10) has:
 (1) a first data communication interface (28) for at least indirect connection of the personal programmable device (10) to a service center (30), and
 (2) a second data communication interface (26), separate from the first data communication interface (28), for the direct wireless connection of the programmable personal device (10) to the programming device (70), and
b. the programming device (70) has:
 (1) a data communication interface (72) for the direct wireless connection of the programming device (70) to the programmable personal device (10),
 (2) a TAN list generator (78) generating a TAN list, and an associated index for each generated TAN, and transmitting the TAN list and each TAN's associated index to:
  (a) the programmable personal device (10), and
  (b) one or more of:
   i. a TAN server (80),
   ii. a personal communication device (100), and
   iii. a printer.

2. The system of claim 1 wherein the programmable personal device (10):
a. determines an index of a TAN for a subsequent programming instruction, and
b. transmits it to the service center (30) after:
 (1) receiving a TAN list with associated indices, or
 (2) execution of a programming instruction.

3. The system of claim 1:
a. further including a TAN server (80), and
b. wherein the programming device (70) includes a second data communication interface (74):
 (1) providing data transmission from the programming device (70) to the TAN server (80), and
 (2) transmitting a generated TAN list to the TAN server (80).

4. The system of claim 3 wherein the TAN server (80) has:
a. a databank (86) containing entries for:
 (1) a user identification,
 (2) a programmable personal device (10):
 (3) a device identification, and
 (4) a message address of an addressable communication device (100),
b. a TAN user interface:
 (1) accepting user inputs,
 (2) assigning the inputs to a user identification, and
 (3) relaying the user identification and assigned user inputs to the TAN server (80)
c. a message interface (90) via which the TAN server (80) may transmit a message to an addressable communication device (100) which is identified by a message address, and
d. a data communication interface (82) receiving data from of the programming device (70),
wherein the TAN server:
I. provides TAN,
II. receives a TAN query assigned to a user identification, and
III. subsequently generates a message containing a TAN and transmits it via the message interface (90) to the addressable communication device (100) assigned via the databank entries to the user identification of the querying user.

5. A system for the remote programming of a programmable personal medical device (10), in particular an implantable medical device such as a cardiac pacemaker, defibrillator, or the like, including:
I. a programmable personal device (10), and
II. a programming device (70),
III. a service center,
wherein:
a. the programmable personal device (10) has:
 (1) a first data communication interface (28) for at least indirect connection of the personal programmable device (10) to a service center (30), and
 (2) a second data communication interface (26), separate from the first data communication interface (28), for the direct wireless connection of the programmable personal device (10) to the programming device (70);
b. the programming device (70) has:
 (1) a data communication interface (72) for the direct wireless connection of the programming device (70) to the programmable personal device (10),
 (2) a TAN list generator (78) generating a TAN list and transmitting it to:
  (a) the programmable personal device (10), and
  (b) one or more of:
   i. a TAN server (80),
   ii. a personal communication device (100), and
   iii. a printer;
c. a service center (30) having:
 (1) a data communication interface (36) for a data communication with the programmable personal device (10), and
 (2) a service user interface (38) connected to the service center (30), the service user interface (38):
  (a) accepting a programming instruction for the programmable personal device (10),
  (b) accepting a manual input of a TAN for the programming instruction,
  (c) appending the TAN to the programming instruction, and
  (e) transmitting the programming instruction and appended TAN to the programmable personal device (10),
and wherein the programmable personal device (10) compares:
a. the TAN transmitted from the service center (30) appended to the programming instruction, and
b. a stored TAN received from the programming device (70),
and executes the programming instruction if the TAN match.

6. The system of claim 5 wherein the service user interface (38) identifies the index of the TAN appended to the programming instruction.

7. The system of claim 6 wherein:
a. the service user interface accepts a TAN query of a user together with a user identification of this user,
b. the service center (30)
 (1) has a second data communication interface (38) providing data exchange from the service center (30) to the TAN server (80), and
 (2) relays a TAN query received via the service user interface to the TAN server (80).

8. The system of claim 6 wherein the service user interface (38) is remotely connected to the service center (30).

9. The system of claim 5 wherein the programmable personal device (10) further compares:

a. the TAN transmitted from the service center (30) appended to the programming instruction, and b. a stored TAN received from the programming device (70), and ignores or erases the programming instruction if the TAN match.

10. The system of claim 5 wherein the TAN list generator (78) of the programming device (70) generates an associated index for each generated TAN and transmits the generated index with each TAN to:

a. the programmable personal device (10), and b. to at least one of:
  (1) a TAN server (80),
  (2) a personal communication device (100), and
  (3) a printer.

11. A system for the remote programming of a programmable personal medical device (10), in particular an implantable medical device such as a cardiac pacemaker, defibrillator, or the like, including:

I. a programmable personal device (10), and
II. a programming device (70),
wherein:

a. the programmable personal device (10) has:
  (1) a programmable controller,
  (2) a memory for storing a TAN list,
  (3) at least one stimulation pulse generator,
  (4) a first data communication interface (10) for at least indirect connection of the programmable personal device (10) to the service center (30),
  (5) a second data communication interface (18) separate from the first data communication interface (10), the second data communication interface (18) providing communication between the programmable personal device (10) and the programming device (70), b. the programming device (70) has:
  (1) a data communication interface (72) for the direct wireless connection of the programming device (70) to the programmable personal device (10),
  (2) a TAN list generator (78) generating a TAN list and transmitting it to:
    (a) the programmable personal device (10), and
    (b) one or more of:
      i. a TAN server (80),
      ii. a personal communication device (100), and
      iii. a printer, and further wherein:
(1) the programmable personal device (10) receives:
  (a) a TAN list via the second data communication interface (18), the TAN list then being stored in the memory,
  (b) a programming instruction via the first data communication interface (16), the programming instruction being received with an associated TAN,
(2) after receipt of a programming instruction, the programmable personal device (10):
  (a) compares the TAN received together with the programming instruction to a stored TAN, and
  (b) only executes the programming instruction if both TAN are identical.

12. The personal device of claim 11 wherein the programmable personal device (10):

a. stores a list of TAN with associated TAN indices, and b. after receiving a TAN list with associated TAN indices or after execution of a programming instruction:
  (1) determines a TAN index of a TAN for a subsequent programming instruction and
  (2) transmits the TAN index via the first data communication interface.

13. A system for the remote programming of a programmable personal medical device (10), in particular an implantable medical device such as a cardiac pacemaker, defibrillator, or the like, including:

a. a programmable personal device (10) having:
  (1) a first data communication interface (28), and
  (2) a second data communication interface (26) separate from the first data communication interface (28);

b. a programming device (70) having a TAN list generator (78) which generates a TAN list and transmits it to:
  (1) the programmable personal device (10) via the second data communication interface (26), and
  (2) a programmer;

c. a service center (30):
  (1) accepting from the programmer:
    (a) a programming instruction for the programmable personal device (10);
    (b) a TAN associated with the programming instruction;
  (2) transmitting the programming instruction and the associated TAN to the programmable personal device (10) via the first data communication interface (28),
  wherein the programmable personal device (10):
  A. defines a TAN for an acceptable programming instruction, and
  B. compares:
    i. the defined TAN, and
    ii. the TAN associated with the programming instruction,
    and executes the programming instruction if the TAN match.

14. The system of claim 13 wherein the TAN defined by the programmable personal device (10) is at least partially defined by the TAN list transmitted from the programming device (70).

15. The system of claim 13 wherein the programmable personal device (10) ignores or erases the programming instruction if the defined TAN and the TAN associated with the programming instruction do not match.

16. The system of claim 13 wherein:

a. the programming device (70) transmits the TAN list to the programmable personal device (10) with a TAN index list, the TAN index list containing a unique TAN index assigned to each TAN within the TAN list;

c. the programmable personal device (10) executes the programming instruction only if the defined TAN is associated with a current TAN index within the TAN index list.

17. A method for the secure programming of a medical implant (10) by use of a programming device (70), the method having the following steps:

a. generating a TAN list;

b. first transmitting the TAN list to the implant (10) via a second data communication interface (26);

c. composing a programming instruction in the programming device (70);

d. appending a TAN from the TAN list to the programming instruction;

e. transmitting the programming instruction and appended TAN to the implant (10) via a first data communication interface (28);

f. comparing the appended TAN and the TAN first transmitted to the implant (10);

g. if the appended TAN and the TAN first transmitted to the implant (10) are identical, executing the programming instruction in the implant (10).

18. The method of claim 17:
a. wherein the TAN list is generated, and transmitted to the implant (10), with associated TAN indices;
b. further including the steps of:
  (1) defining an index within the implant (10);
  (2) determining, from the TAN list, the TAN having the index defined by the implant (10), this TAN being the TAN appended to the programming instruction.

19. The method of claim 17 further including the step of indicating whether the programming instruction has been executed.

20. The method of claim 17 wherein if the appended TAN and the TAN first transmitted to the implant (10) are not identical, the programming instruction is ignored or erased.

* * * * *